United States Patent
Jin

(10) Patent No.: US 9,145,577 B2
(45) Date of Patent: Sep. 29, 2015

(54) LIPOPROTEIN LIPASE ASSAY

(75) Inventor: Weijun Jin, Brooklyn, NY (US)

(73) Assignee: The Research Foundation of State University of New York, Albany, NY (US)

(*) Notice: Subject to any disclaimer, the term of this patent is extended or adjusted under 35 U.S.C. 154(b) by 168 days.

(21) Appl. No.: 13/206,682

(22) Filed: Aug. 10, 2011

(65) Prior Publication Data

US 2012/0064556 A1    Mar. 15, 2012

Related U.S. Application Data

(60) Provisional application No. 61/372,325, filed on Aug. 10, 2010.

(51) Int. Cl.
| | | |
|---|---|---|
| *C12Q 1/34* | (2006.01) | |
| *C12Q 1/00* | (2006.01) | |
| *C12Q 1/44* | (2006.01) | |
| *C12Q 1/56* | (2006.01) | |
| *C12N 9/18* | (2006.01) | |

(52) U.S. Cl.
CPC .. *C12Q 1/44* (2013.01); *C12Q 1/00* (2013.01); *C12Q 1/34* (2013.01); *C12Q 1/56* (2013.01); *C12N 9/18* (2013.01); *G01N 2333/914* (2013.01); *G01N 2333/918* (2013.01)

(58) Field of Classification Search
CPC .............. C12N 9/18; C12N 9/16; C12N 9/14; C12Q 1/44; C12Q 1/34; C12Q 1/61; C12Q 1/00; G01N 33/92; G01N 2333/916; G01N 2333/914; G01N 33/44; C12Y 301/01034
See application file for complete search history.

(56) References Cited

PUBLICATIONS

Mitnaul et al., Journal of Lipid Research, 48:472-482, 2007.*
Boberg et al., Lipids, 5(5):452-456, 1970.*
EnzChek Lipase Substance, Product information from Life Technology (previous Invitrogen), retrieved on May 19, 2013 from the internet: http://products.invitrogen.com/ivgn/product/E33955.*
Wikipedia—Lipoprotein lipase, retrieved on May 19, 2013 from the internet: http://en.wikipedia.org/wiki/Lipoprotein_lipase.*
Debapriya Basu, Jahan Manjur, Weijun Jin, Determination of lipoprotein lipase activity using a novel fluorescent lipase assay, J. Lipid Res. 2011 52:(4) 826-832. First Published on Jan. 26, 2011, doi:10.1194/jlr.D010744.

* cited by examiner

*Primary Examiner* — Jennifer McDonald
*Assistant Examiner* — Qing Xu
(74) *Attorney, Agent, or Firm* — Scully, Scott, Murphy & Presser, P.C.

(57) ABSTRACT

The present invention is directed to a method and kit for the measurement of LPL. The method comprises several steps that effect a measurement of a level of LPL activity. The kit comprises several elements that effect the measurement of a level of LPL activity.

9 Claims, 7 Drawing Sheets

LIPOPROTEIN LIPASE ASSAY

CROSS REFERENCE TO RELATED APPLICATIONS

This application claims the benefit of U.S. Provisional Patent Application No. 61/372,325 filed on Aug. 10, 2010, the entire contents of which are incorporated herein by reference.

STATEMENT REGARDING FEDERALLY SPONSORED RESEARCH OR DEVELOPMENT

This application was made with government support under the United States Department of Health & Human Services, National Institutes of Health, grant number HL081861. The Government has certain rights in the application.

FIELD OF THE INVENTION

The invention relates generally to the field of assays and their use in determining Lipoprotein Lipase activity levels.

BACKGROUND OF THE INVENTION

Lipoprotein lipase (LPL) is the rate-limiting enzyme controlling plasma triglyceride (TG) levels by hydrolyzing TG into free fatty acids and glycerol. This biological process is critical for energy mobilization and utilization and has a variety of clinical implications. LPL is specifically found in endothelial cells lining the capillaries.

Mutations that cause LPL deficiency result in type 1 hyperlipoproteinemia, hypertriglyceridemia or other disorders involving lipoprotein metabolism.

Traditionally, a variety of assays have been employed for measuring LPL activity. Generally, they can be divided into two formats, coupled and uncoupled assays. Coupled assays involve a chain of enzymatic reactions and can be used to indirectly determine LPL activity in relatively simple biological specimens. Uncoupled assays can further be divided to two groups, non-homogeneous and homogeneous assays.

Non-homogeneous assays require quantifying lipolytic products, typically by monitoring fatty acids liberated by LPL. Non-homogeneous assays are tedious and have a low throughput. For example, a radiolabeled triolein substrate is typically used in radiometric assays for measuring LPL activity. The labeled fatty acids released by LPL must be separated from the labeled triolein, before quantification, through a series of organic extraction procedures. Another common non-homogeneous assay used is a titratimetric method, which is not very sensitive.

Homogeneous assays are typically fluorescence-based and rely on changes in the fluorescence properties of a substrate upon hydrolysis. Traditionally, several naturally fluorescent groups including Dansyl, NBD or Pyrene have been incorporated into TG substrates for detecting LPL activity. However, the high background noise created by using these groups limits their wide use. Coumarin derivatives are one fluorescent group which only fluoresce after they are converted to lipolytic products, but these derivatives suffer from many problems such as instability and non-specific hydrolysis by enzymes other than LPL. Further, they do not resemble LPL's native substrate, triglyceride.

What is desired is an easy to use, sensitive, environmentally friendly, real-time LPL assay which does not require purification and will provide accurate results at a high throughput.

SUMMARY OF THE INVENTION

The present invention is directed to a method and kit for the measurement of LPL. The method comprises the following steps; administering a dosage of an anti-coagulant to the subject, gathering the biological sample, adding the biological sample to a well of a well plate, adding a first buffer to the well plate, adding a second buffer to the well plate, adding a substrate to the well plate, incubating the well plate, measuring the fluorescence of the material within the well plate, and correlating the measured fluorescence to a level of LPL activity. The kit comprises the following elements; an anti-coagulant, a well plate, a first buffer, a second buffer, a substrate, and a correlator.

BRIEF DESCRIPTION OF THE DRAWINGS

The present invention will be better understood by reference to the following drawings of which.

DETAILED DESCRIPTION OF THE INVENTION

Figure 1:
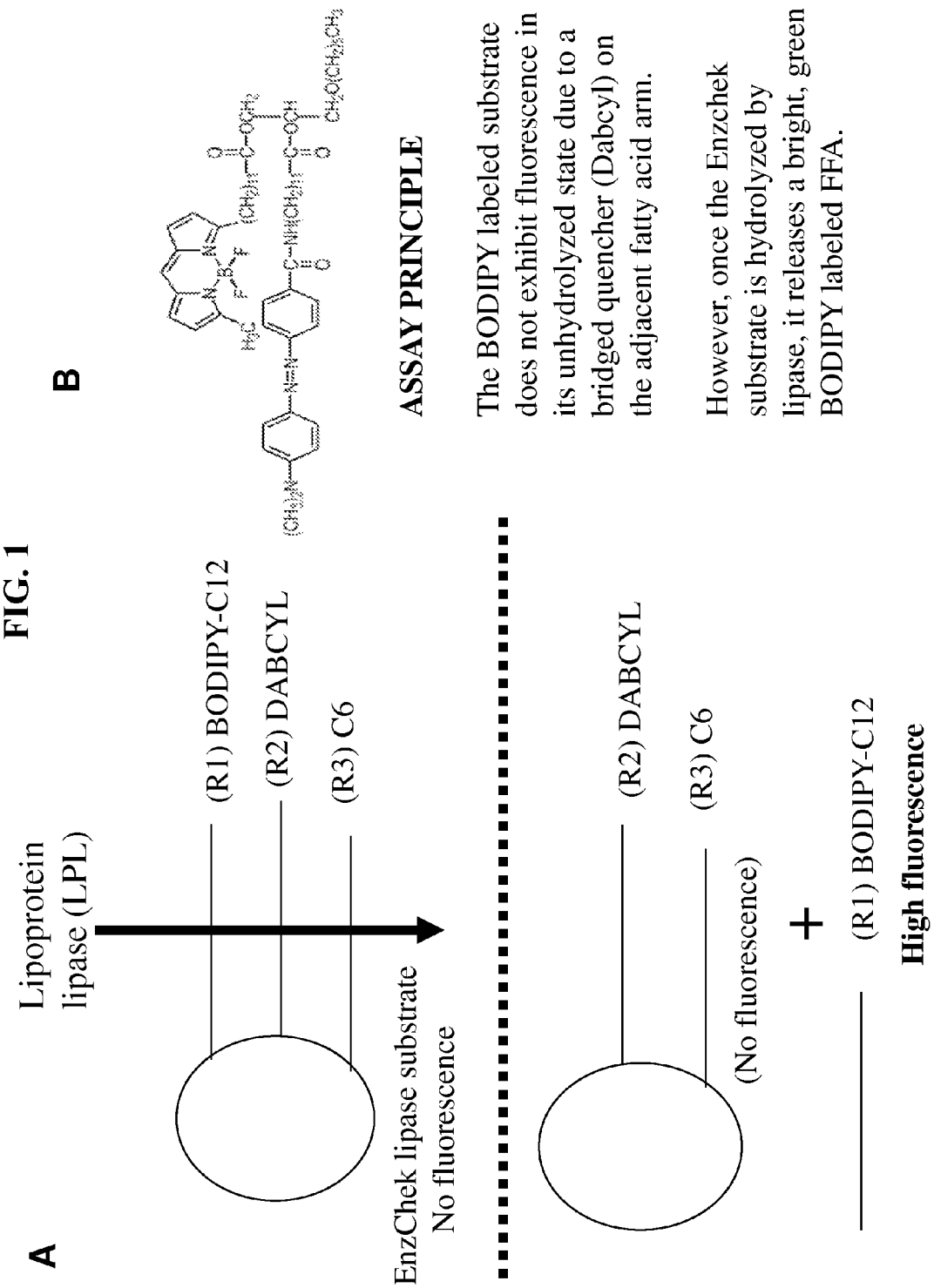
FIG. 1 is an illustration of lipase hydrolysis.

The methods and kits of the present invention are improvements over traditional methods and assay kits which are not sensitive, are time consuming and contain material which is not easily disposed of. The improvements are, inter alia, a sensitive assay method which has a high throughput because of short reaction times and purification of samples not being required; and does not contain material, such as radioactive material, which must be handled and discarded in a very careful manner.

In one embodiment of the present method to detect the activity of lipoprotein lipase (LPL) in a biological sample of a subject, a dosage of anti-coagulant is first administered to the subject. The subject can include any suitable animal, including mammals, domestic animals, livestock, poultry and humans. This anti-coagulant can be any suitable anti-coagulant, such as heparin, cytokine tumor necrosis factor (TNF), hylomicrons, very low density lipoproteins (VLDL), and free fatty acids such as oleic acid bound to bovine serum albumin, among other suitable anti-coagulants. When the anti-coagulant is heparin, the suitable dosage administered is typically about 10 units/kg if administered intravenously and about 400 units/kg if administered via intraperitoneal injection.

The anti-coagulant can be administered in any suitable method including orally, intravenously, subcutaneously or combinations of these administration routes. After the anti-coagulant is administered, a biological sample is collected from the subject. The biological sample can be a blood sample, which can be gathered by a hypodermic needle or any other suitable instrument. In one embodiment, where the biological sample is a blood sample, the blood sample can be centrifuged to separate its components. The blood sample can be centrifuged for any suitable length of time and at any suitable speed, including about 10 minutes at about 7000 G.

Upon completion of the centrifugation, the plasma of the blood sample will be separated from the other blood components and can be collected.

Once the biological sample has been gathered from the subject, and has either been subjected to further separation or not, the biological sample is added to a well of a well plate. Any suitable well plate can be used, including a 96 well plate which is commercially available from many sources, including Costar®.

After the biological sample has been added to the well of the well plate, a first buffer is added. The first buffer can comprise NaCl, Tris-HCl (PH=8.0) and fatty acid free BSA. The concentrations of these components can be at any suitable level, such as about 0.6 M for NaCl, about 80 mM for Tris-HCl and about 6% for fatty acid free BSA. After the first buffer is added to the well of the well plate, a second buffer is added to the same well. The second buffer can comprise n-Hexadecyl-N,N-dimethyl-3-ammonio-1-propanesulfonate or Zwittergent®. The concentration of Zwittergent® can be at any suitable level, such as about 0.0125%.

Following the addition of the second buffer, a substrate is added to the same well. The substrate can comprise an EnzChek® lipase substrate which is composed of a 4,4-difluoro-5-methyl-4-bora-3a,4a-diaza-s-indacene-3-dodecanoic acid (BODIPY) dye and a quencher in a TG backbone. The substrate, which includes the BODIPY can be commercially purchased from Invitrogen™ with an emission/excitation of 500/510. BODIPY has a narrow emission bandwidth around 515 nm, a high extinction coefficient ($\epsilon$>8000/(cm)(M)) and a quantum yield which approaches 1. The BODIPY spectrum is relatively insensitive to solvent polarity and is stable in the physiological pH range, which is an advantage over 7-nitrobenz-2-oxa-1,3-diazole (NBD) labeled substrates. BODIPY has a sufficient photostability and can be handled without need of being shielded from the light. BODIPY also does not have an ionic charge and will not interfere with the solubility of TG into which it is incorporated.

In the presence of the quencher, the substrate is a stable and nonfluorescent compound in an un-reacted state, but produces a green fluorescent BODIPY labeled fatty acid in the presence of LPL. Lipase hydrolysis of the ns-1 ester severs the BODIPY labeled fatty acid, removing it from proximity to the Dabcyl quencher and resulting in bright green fluorescence, as further shown in FIG. 1. The principle of this assay is that the BODIPY labeled substrate does not exhibit fluorescence in its unhydrolyzed state due to a bridged quencher (Dabcyl) on the adjacent fatty acid arm. However, once the EnzChek substrate is hydrolyzed by lipase, it releases a bright green BODIPY labeled FFA.

LPL is known to attack preferentially at position 1 of TGs. Thus the EnzChek substrate can be used for the accurate and sensitive detection of LPL activity in solution. Thus, the BODIPY dye can be used for accurate and sensitive detection of LPL activity in solution without the need of a purification step.

Figure 2:
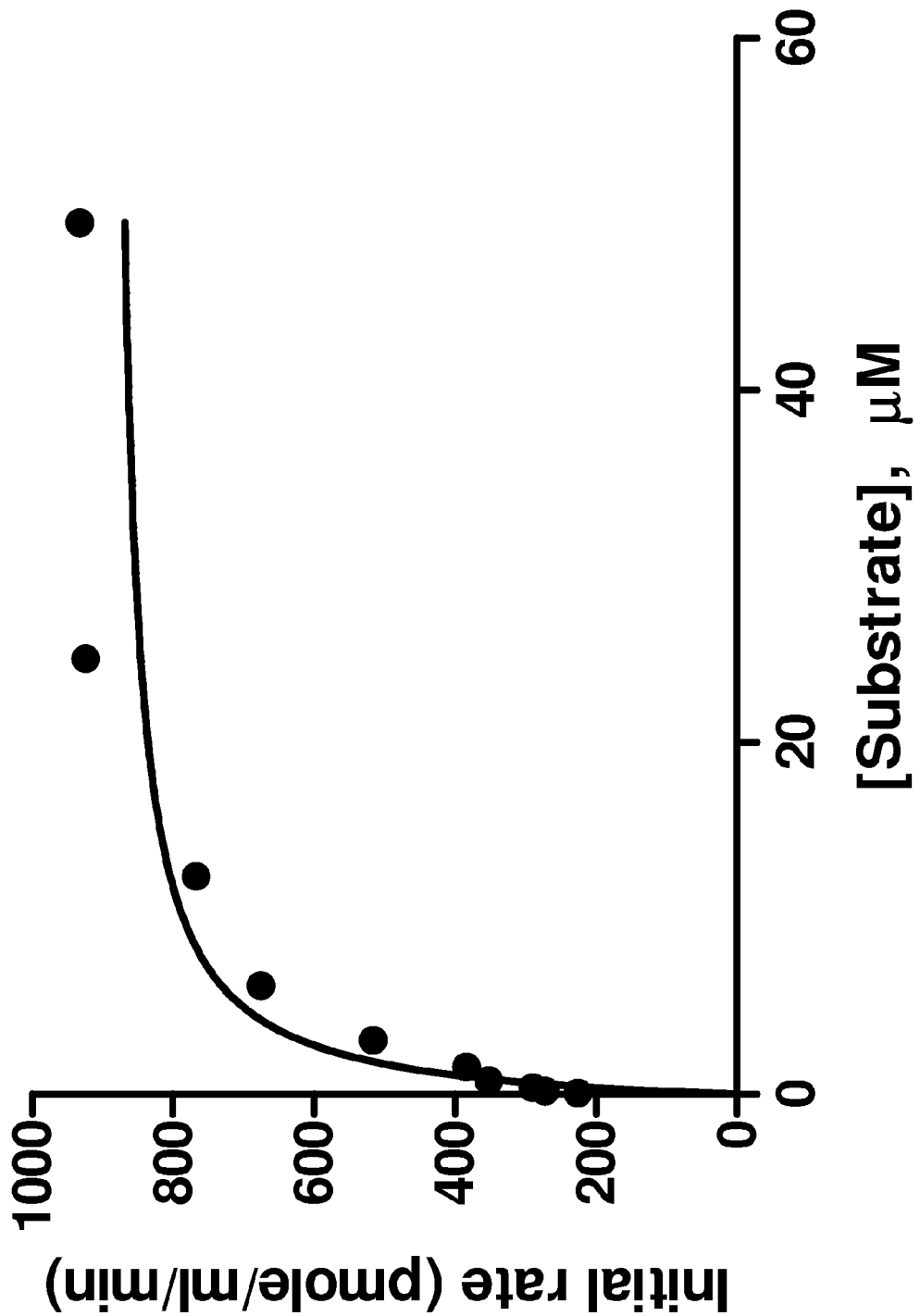
FIG. 2 is an illustration of LPL activity with an EnzChek substrate.

Fluorescence increase with time was determined using a fixed amount of LPL (175 ng per well) and increasing amounts of the EnzChek substrate at 37° C. in 100 µL total volume in the presence of 0.15 M NaCl, 20 mM Tris-HCl, pH 8.0, 0.0125% Zwittergent and 1.5% fatty acid free BSA. Initial rates were then plotted against substrate concentration and followed Michaelis-Menten kinetics, as shown in FIG. 2. In FIG. 1, background substrate hydrolysis was deducted from each measurement, initial rate was plotted against substrate concentration and each data point is the mean of triplicate determinations. Nonlinear regression analysis was carried out to calculate the kinetic parameters: Km=1.36 M, Vmax=0.89 µmol/ml/min and Kcat=0.0255 µmol/mL/min. The uncatalyzed background hydrolysis rate of the EnzChek substrate was low, approximately 0.1 pmol/min.

Figure 3:
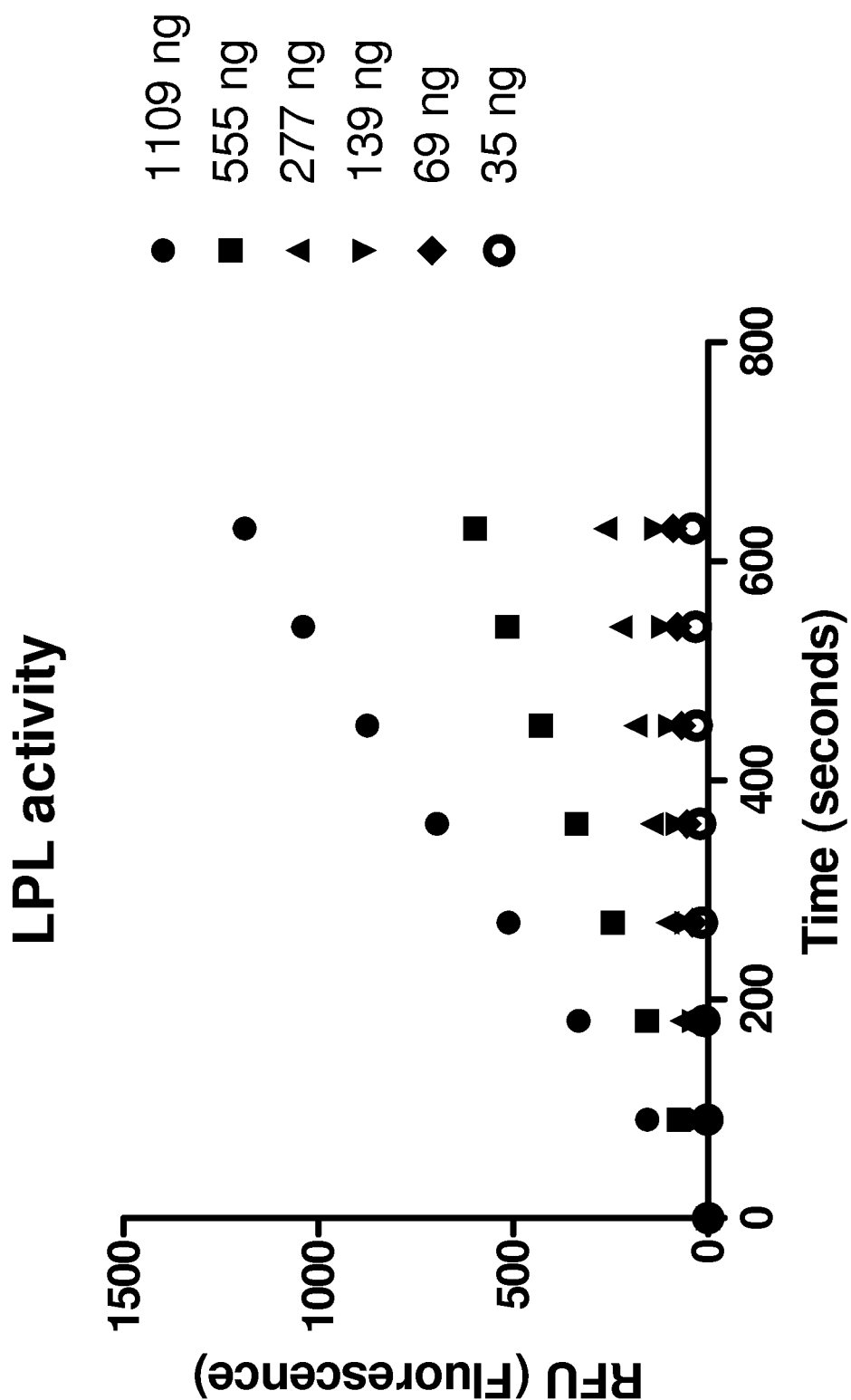
FIG. 3 is an illustration of the upper limit of the LPL concentration range.
Figure 4:
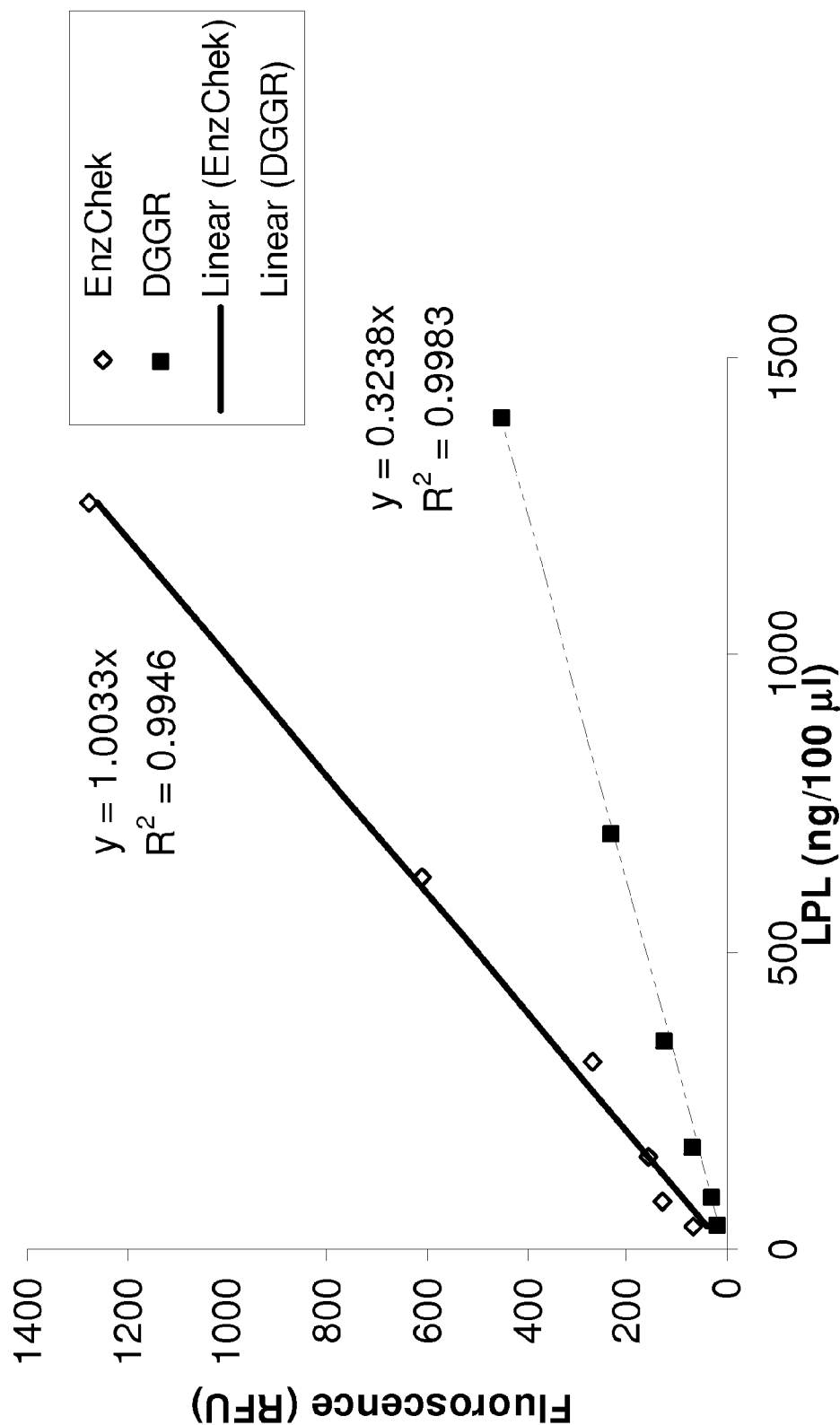
FIG. 4 is an illustration of the comparison of LPL activities using EnzChek and DGGR substrates.

To determine the optimal concentration for this assay, different amounts of LPL were titrated in wells using a fixed amount of the EnzChek® substrate (0.62 µM). The reaction progress curves are shown in FIG. 3. In FIG. 3, background substrate hydrolysis was deducted from all measurements and each data point is the mean of triplicate determinations. With this substrate concentration, the time dependent fluorescence increase was linear at each of the enzyme concentrations tested, including the highest, 1109 ng/100 µL. Taking advantage of this linearity, the 540 second time point (9 minutes) in each assay was used to plot initial rate vs LPL concentration For the reaction progress curves, the initial velocity at 10 minutes was determined and plotted against LPL dose, there was a dose-dependent increase in velocity with increasing amounts of LPL, as can be seen in FIG. 4. FIG. 4 is further described in Example 2 below. This linear increase of velocity as the function of LPL concentration sustained at least about 30 minutes, although the highest signal to noise ratio of about 30 and correlation coefficient were obtained at approximately 10 minutes following the reaction. Based on this information, this method can also be used as an endpoint assay by measuring the fluorescent signal at about 10 minutes after the beginning of an incubation step.

Figure 5:
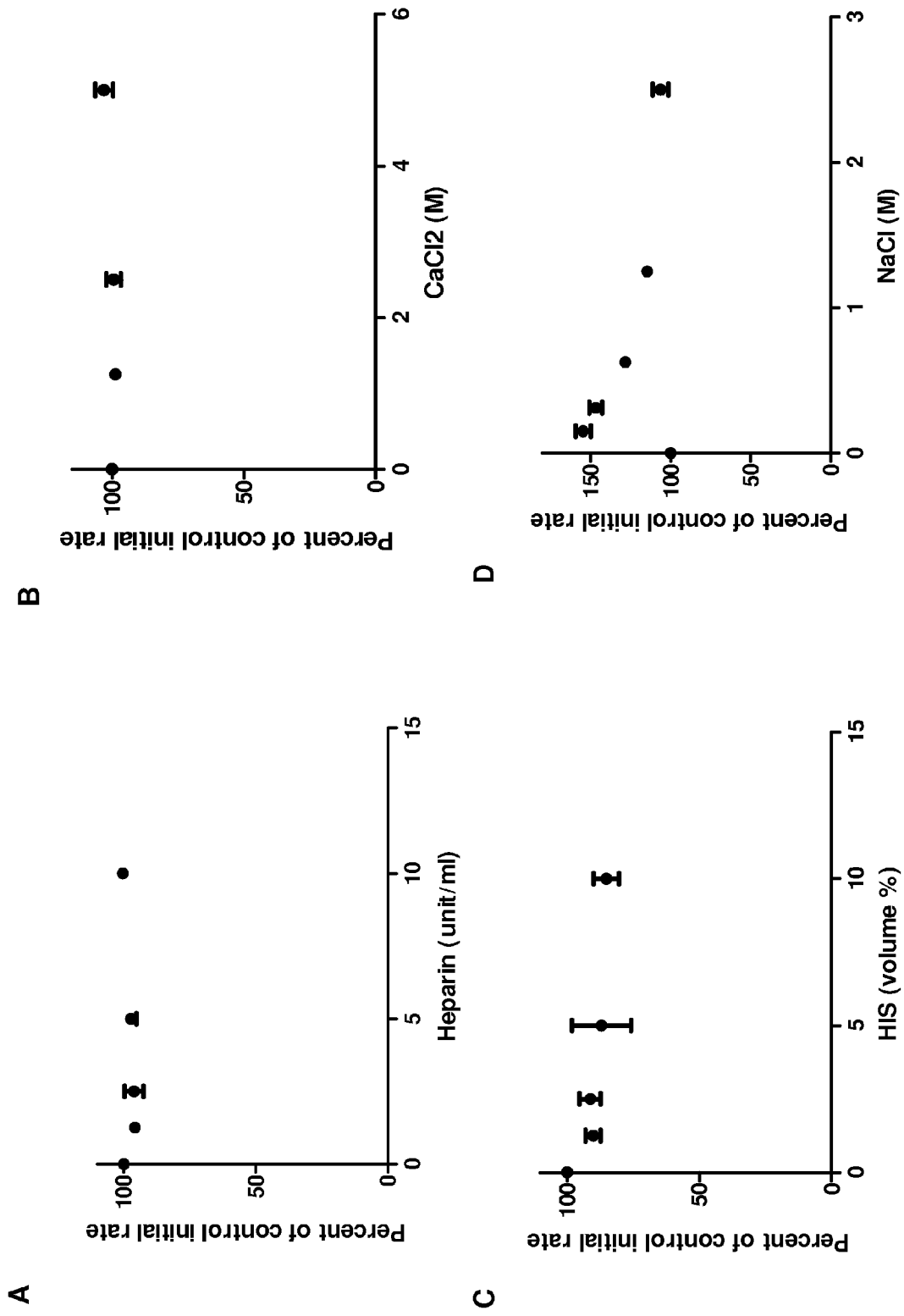
FIGS. 5A-5D are illustrations of LPL activity.

The effects of components that may be present in biological LPL samples and affect the assay were also evaluated and illustrated in FIG. 5. Addition of heparin and calcium increased LPL activity by about 6% over the concentration ranges tested, shown in FIGS. 5A and 5B, while HIS, added from 0-10% decreased the activity by about 12%, shown in FIG. 5C. Addition of NaCl increased the reaction rate, shown in FIG. 5D, with the highest rate, 46% higher than that without salt, occurring at 0.15 M. As NaCl was increased further, the reaction rate dropped, but even at 2.5 M was not reduced to that without NaCl. This implies that there is no inhibition of LPL activity by NaCl if apoC-II is not used in the assay.

Following the addition of the substrate, the well plate is incubated at a temperature for a period of time. In one embodiment, the temperature is kept constant at about 37° C. for about 10 minutes. In other embodiments, the temperature can range from about 25° C. to about 40° C. with the amount of time ranging from about 2 minutes to about 2 hours.

Following the incubation period, the fluorescence of the material in the well plate is measured. Fluorescence can be measured in a fluorescence plate reader or a standard fluorometer. The reaction has an excitation/emission maxima of about 482 nm to about 515 nm. The level of fluorescence is evidence of the level of LPL activity, and the level of LPL activity can be determined by correlating it with the measured level of fluorescence. This correlation is aided by use of the following formula:

$$LPL \text{ activity units} = \frac{\text{Measured Fluorescence }(RFU)}{175.98}$$

This formula is based on the information gathered and shown in FIG. 3. The level of LPL activity can then be used to determine a baseline measurement of and changes to the subject's triglyceride (TG) level.

This method produces an assay which provides a signal to background ratio of about 30, a coefficient of variation (CV)

below 5% and the statistical parameter Z of 0.8. The method can be used to screen for both catalytic and non-catalytic inhibitors as well as activators of LPL and other TG-hydrolyzing enzymes.

The kit to be used with the above described method can be set up in a mix-to-go format. One advantage of the kit is that it does not need the preparation of traditional substrate emulsions. Due to the stability of all of the components, the kit can be used in many different scenarios, including measuring lipase activity in patients with hypertriglyceridemia, and the analysis of different lipases that can be found in serum only under pathological conditions, such as in acute pancreatitis.

To be able to practice the above described method, the kit would include several components. The kit would include a sufficient amount of an anti-coagulant, for example heparin, for a correct dosage based on the individual subject. The kit could also include an instrument to administer the anti-coagulant, such as, for example, a hypodermic needle. The instrument could be used to administer the anti-coagulant intravenously, subcutaneously, or be used for both. The kit could also include an instrument to gather a biological sample, such as, for example, a hypodermic needle.

The kit would include a well plate having at least one well. The well or wells of the well plate would be of suitable size to hold a biological sample and other components in the kit including the first buffer, second buffer and the substrate. The kit would further include a first buffer. The first buffer could comprise a mixture of NaCl, Tris-HCl and fatty acid free BSA. The concentrations of these components would be about 0.6 M NaCl, 80 mM Tris-HCl and 6% for fatty acid free BSA. The kit would further include a second buffer. The second buffer could comprise n-Hexadecyl-N,N-dimethyl-3-ammonio-1-propanesulfonate or Zwittergent®. The concentration of Zwittergent® can be at any suitable level, such as about 0.0125%.

Further included in the kit is a substrate. The substrate can be EnzChek® lipase substrate which is composed of a 4,4-difluoro-5-methyl-4-bora-3a,4a-diaza-s-indacene-3-dodecanoic acid (BODIPY) dye and a quencher in a TG backbone. To perform the assay contained in the kit, other instruments are used, such as, for example, an incubator, a fluorometer or a plate reader. These instruments would be present in a laboratory or clinical setting for performance of the assay contained in the kit.

A correlator can also be included in the kit. This correlator represents how a fluorescence measurement can be converted to LPL activity. The correlator can be any suitable graph, chart, program or formula card which allows an administrator who is using the kit to convert the measured fluorescence value to an LPL activity value. In one embodiment, the correlator can be a chart, either on paper or as part of a computer program. This chart will have an x and y axis along with a value line which represents RFU divided by about 175.98 over a large range of values. Once a specific RFU is recorded through use of the kit, it can be matched to the corresponding LPL activity unit on the y axis of the chart. In another embodiment, the correlator could be a calculator or computer program which divides the specific, measured RFU values by about 175.98, thus producing the corresponding LPL activity.

The LPL lipase assay described has a "mix and go" format and does not require preparation of traditional substrate emulsions which have limited stability. It fulfills several needs of a high throughput assay for LPL: signal to background ration of approximately 30:1, coefficient of variation below 5% and the statistical parameter Z is about 0.8. The assay is suited for high throughput screening of both activators and catalytic/non-catalytic inhibitors of LPL and can be used to assay other TG hydrolyzing enzymes.

While the present invention has been described in particular embodiments, it should be appreciated that the present invention should not be construed as limited by such embodiments, but rather construed according to the below claims.

Example 1

In the following example, one embodiment of using a lipoprotein lipase assay is described.

In this embodiment, all reagents were purchased from Sigma-Aldrich unless otherwise stated. The specific activity of lipoprotein lipase (LPL) used for the experiments was about 5,700 units/mg. The boron-dipyrromethene (BODIPY)-labeled triglyceride (TG) analog EnzChek® and 4,4-difluoro-5-methyl-4-bora-3a,4a-diaza-s-indacene-3-dodecanoic acid (BODIPY 500/510 C1, C12) were purchased from Invitrogen™. Heat inactivated rat serum (HIS) was generated according to standard procedures.

The SpectraMax® M2 plate reader and SoftMax® Pro 5 from MDS Analytical Technologies were used for fluorescent measurements. The optimal wavelength was determined to be 482 nm/515 nm (Emission/Excitation, Em/Ex) with a 495 nm filter cutoff. The linear capacity of these instruments is up to 2.4 μmol/well. An assay was performed in a black 96-well plate from Costar® in the presence of 0.15 M NaCl, 20 mM Tris-HCl, and 0.0125% Zwittergent® and 1.5% fatty acid free BSA. A 4× working solution was freshly prepared with 0.6 M NaCl, 80 mM Tris-HCl and 6% fatty acid free BSA. The background hydrolysis rate of the substrate was about 1 pmol/min. In the typical assay, the amount of substrate hydrolyzed was less than about 5% of the available substrate.

Conditioned media was generated by transfection in HEK293 cells as is known. Medium obtained from cells expressing from an empty vector was included as a control for the LPL assay. No lipase activity was detected in the control medium. Pre and post-heparin mouse serum was obtained from blood drawn 5 minutes after the injection of 10 units heparin per kg body weight of the mouse.

Enzymatic parameters were calculated using unquenched the BODIPY-C12 probe, the reaction rate in pmol/min was calculated. The rate of hydrolysis as determined from the continuous increase in fluorescence intensity is equal to the rate of separation of the quencher fatty acid from the substrate. Enzymatic parameters such as $V_{max}$, $K_m$, $K_{cat}$, detection limit, Z factors and correlation coefficient were calculated based on the standard definition of those parameters. The data is presented as mean plus standard deviation of three replicates and described below in Example 2 for a comparison of the inventive method and a traditional assay.

Figure 7:
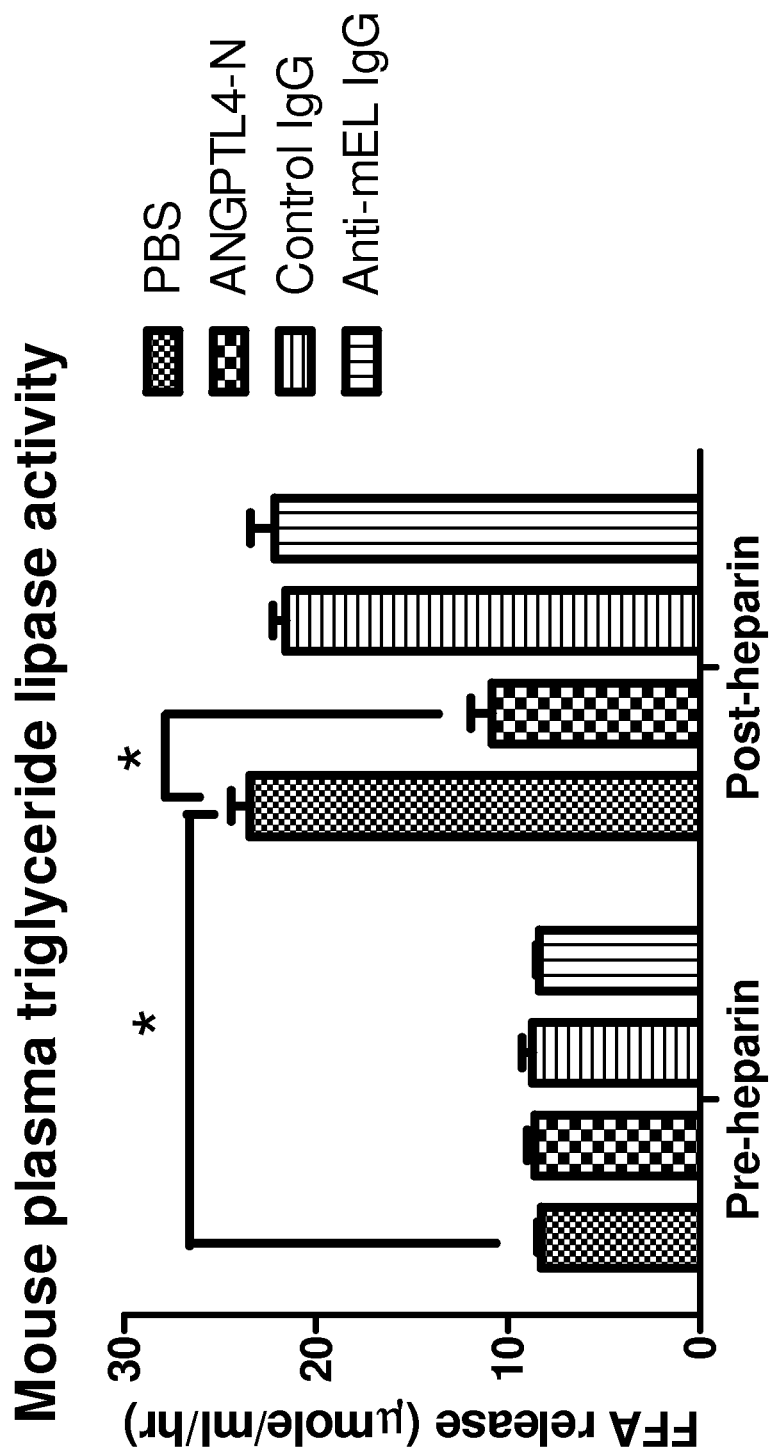
FIG. 7 is an illustration of the measurement of TG lipase activities in mouse plasma.

The results measured upon conducting the steps of the above example in post-heparin mouse serum can be seen in FIG. 7. Post heparin plasma (PHP) from mice was measured using the above described assay under standard conditions and in triplicate to determine plasma lipase activity. FIG. 7 indicates that significant TG lipase activity was detected using the present assay in both pre- and post-heparin mouse plasma, with the post heparin activity being significantly higher. Since, in addition to LPL, the substrate is also hydrolyzed by endothelial lipase (EL) and hepatic lipase (HL), the contributions of these lipases to the control group results were evaluated using lipase-specific inhibitors.

Pre- and post-heparin plasma samples (1 μL) were incubated on ice for 30 minutes with one of the following: phosphate buffered saline (PBS), ANGPTL4-N, antibodies AntimEL IgG or Control IgG, prior to analysis as described in connection to FIG. 2. The final concentrations in the assays of ANGPTL4-N and each antibody were 40 nM and 20 μg/mL, respectively. Background substrate hydrolysis was deducted from each measurement. Free Fatty acid, (FFA) released are the mean+/−standard deviation of triplicate repeats, p<0.001. The experiment was repeated three times with similar results.

FIG. 7 shows the assay detecting fluorescence, which can then be used to determine plasma lipase activity, in PHP samples from mice in a time dependent manner. Since LPL is a major triglyceride lipase in PHP, the figure is indicative of the detection of plasma LPL activity by the assay.

Example 2

The inventive method of measuring the activity of LPL as described above was compared to a traditional 1,2-o-dilauryl-rac-glycero-3-glutaric acid-(6'-methylresorufin) ester (DGGR) assay for measuring LPL activity. Samples tested using the DGGR assay were purified prior to incubation, the samples tested using the inventive method were not purified. The results can be seen in FIG. 4. In FIG. 4, initial rates were obtained using 9 minute, single point fluorescence measurements at increasing substrate concentrations. The EnzChek assay was carried out under conditions described in connection with FIG. 2. Background substrate hydrolysis was deducted from all measurements. Data were analyzed by linear regression, each data point is the mean of triplicate determinations, the assay was carried out three times with similar results.

The same batch of purified LPL was used for both assays. Both assays were linear in detecting LPL activity from 1-8 units of LPL per well. However, the slope for the inventive method was steeper, which is indicative of a more sensitive assay. The detection limit for the DGGR assay was 0.3 units of LPL, whereas the detection limit for the inventive method was about 0.003 units. The DGGR substrate has limited solubility in the assay buffer and is precipitated after only one week, whereas the substrate of the inventive method has a longer shelf life.

Example 3

The inventive method of measuring the activity of LPL was also compared to a traditional assay using a Pyrene labeled TG substrate. Based on the difference in fluorescence properties between a Pyrene substrate and the BODIPY substrate of the inventive method, the inventive assay is about five times more sensitive. One disadvantage of the traditional Pyrene substrate is that it is water soluble and cannot be used to study the interfacial activation of LPL, as can the substrate of the inventive method. Another disadvantage is that the autofluorescence derived from plasma proteins is in a range of 300 nm to 410 nm and overlaps with the spectra of Pyrene (Excitation/emission 342/400 nm), thereby interfering with the results. In contrast, the BODIPY substrate used in the inventive method has an excitation/emission of 500/510 nm, which is out of the range of plasma proteins. This characteristic allows the assay of the present method to be better suitable for biological samples in which protein concentrations vary.

Example 4

ANGPTL4, an endogenous inhibitor of LPL, irreversibly converts the active LPL homodimer into inactive monomers. To determine whether the conditions of the assay are such that the two forms of the enzyme are maintained and can be differentiated by the biological activity of the lipase, two conditioned media were generated containing human LPL and ANGPTL4 respectively.

Conditioned human LPL medium (25 μL) was mixed with control medium (25 μL) or conditioned human ANGPTL4 medium (25 μL) and held on ice for 30 minutes prior to addition to LPL activity assays measured using the EnzChek assay as described in connection to FIG. 2 with 0.62 μM EnzChek substrate or the radiometric triolein assay as described above.

Figure 6:
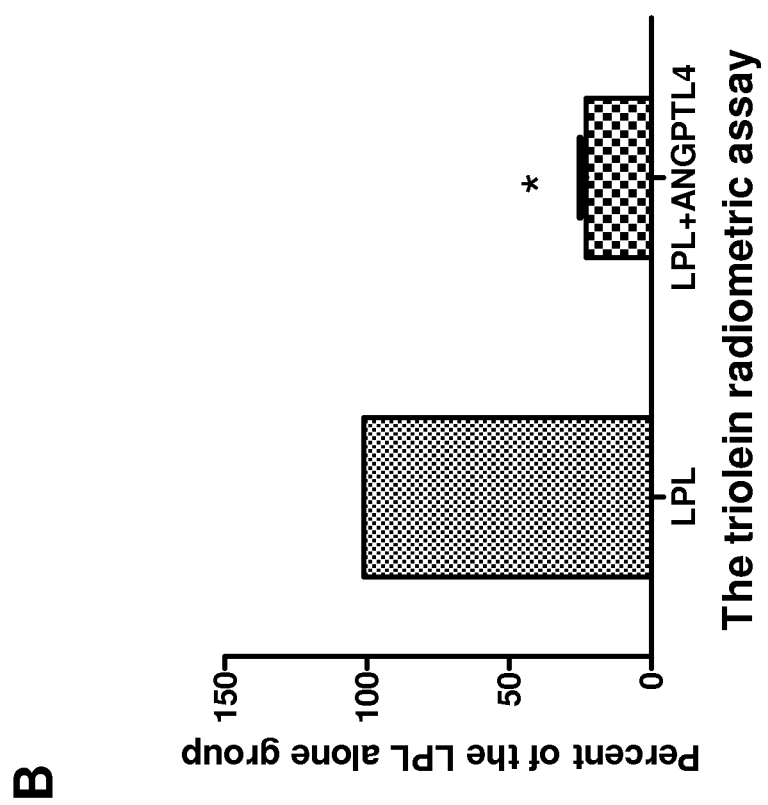
FIGS. 6A and 6B are illustrations of the measurement of human LPL activity.
Figure 6:
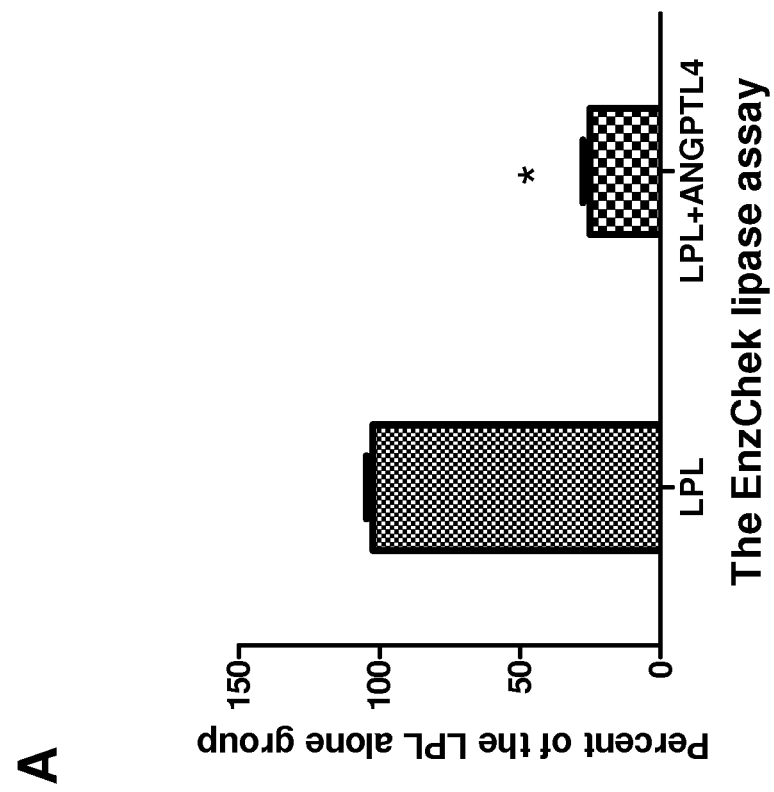

As shown in FIG. 6A, a mixture of the ANGPTL4 conditioned media with that containing LPL inhibited the LPL activity (p<0.05). A comparable result was obtained with the same samples using the conventional radiolabeled triolein assay, as shown in FIG. 6B. Background substrate hydrolysis was deducted from each measurement. LPL activity is expressed as a percentage of the activity measured in the absence of ANGPTL4. The values are the mean+/−standard deviation in triplicate repeats, p<0.05. Thus, the EnzChek substrate assay is valid for measuring human LPL activity in conditioned media.

What is claimed is:

1. A method for detecting activity of lipoprotein lipase in a biological sample of a subject comprising:
   administering a dosage of an anti-coagulant to the subject;
   gathering the biological sample;
   adding the biological sample to a well of a well plate;
   adding a first buffer to the well of the well plate, wherein the first buffer comprises 0.15 M NaCl, 20 mM Tris-HCl and 1.5% fatty acid-free BSA;
   adding a second buffer to the well of the well plate, wherein the second buffer comprises 0.0125% Zwittergent;
   adding a fluorescent substrate to the well of the well plate, wherein the substrate is 0.62 μM 4,4-difluoro-5-methyl-4-bora-3a,4a-diaza-s-indacene-3-dodecanoic acid (BODIPY) dye and a quencher in a TG backbone, and wherein the biological sample, first buffer, second buffer and substrate form a mixture;
   incubating the well plate;
   measuring a fluorescence signal of the mixture within the well of the well plate to obtain a measured fluorescence signal; and
   correlating the measured fluorescence signal to a level of LPL activity.

2. The method of claim 1, wherein the anti-coagulant is heparin.

3. The method of claim 1, wherein the anti-coagulant is administered intravenously, subcutaneously or a combination of intravenously and subcutaneously.

4. The method of claim 1, wherein the well plate is incubated for a period between about 2 minutes to about 2 hours.

5. The method of claim 4, wherein the well plate is incubated for about 10 minutes.

6. The method of claim 1, wherein the biological sample is a blood sample.

7. The method of claim 1, wherein the biological sample is a plasma portion of a blood sample.

8. The method of claim 1, wherein the measured fluorescence signal-to-noise ratio (SNR) is about 30.

9. The method of claim 8, wherein the SNR is about 30 after the well plate is incubated for about 10 minutes.

* * * * *